United States Patent
Yeh et al.

(10) Patent No.: US 7,659,362 B2
(45) Date of Patent: Feb. 9, 2010

(54) METAL-BINDING MOTIF COMPOSITIONS AND METHODS

(75) Inventors: Kuo-Chen Yeh, Hsin-Chu (TW); Cheng-Che Sage Kung, Taoyuan County (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 11/420,881

(22) Filed: May 30, 2006

(65) Prior Publication Data

US 2007/0281333 A1 Dec. 6, 2007

(51) Int. Cl.
*A61K 38/00* (2006.01)
*C07K 14/81* (2006.01)
(52) U.S. Cl. .................... 530/300; 514/6; 514/400; 435/69.1; 435/320.1; 435/325
(58) Field of Classification Search ................. 530/300; 435/69.1, 325, 320.1; 514/6, 400; 536/23.5
See application file for complete search history.

(56) References Cited

U.S. PATENT DOCUMENTS

2006/0029942 A1  2/2006  Yang

FOREIGN PATENT DOCUMENTS

WO  WO 01/72771 A2 * 10/2001

OTHER PUBLICATIONS

Benson et al. "Rational design of nascent metalloenzymes". PNAS 97(12):6292-6297, Jun. 2000.
She et al. "Identification of metal-binding proteins in human hepatoma lines by immobilized metal affinity chromatography and mass spectrometry". Molecular & Cellular Proteomics2:1306-1318, 2003.
Baltzer et al. "Emerging principles of de novo catalyst design" Current Opinion in Biotechnology 12:355-360, 2001.
Ghosh et al. "Probing metal—protein interactions using a de novo design approach". Current Opinion in Chemical Biology 9:97-103, 2005.
Lu. "Design and engineering of metalloproteins containing unnatural amino acids or non-native metal-containing cofactors". Current Opinion in Chemical Biology 9:118-126, 2005.
Arnesano et al. "The unusually stable quaternary structure of human Cu,Zn-superoxide dismutase 1 is controlled by both metal occupancy and disulfide status", Journal of Biological Chemistry 279(46):47998-48003, 2004.
Rojas et al. "De novo heme proteins from designed combinatorial libraries". Protein Science 6:2512-2524, 1997.
Moffet et al. "Peroxidase activity in heme proteins derived from a designed combinatorial library". J. Am. Chem. Soc. 122;7612-7613, 2000.
Wei et al. "Enzyme-like proteins from an unselected library of designed amino acid sequences". Protein Engineering, Design & Selection 17(1):67-75, 2004.
Pinto et al. "Construction of a catalytically active iron superoxide dismutase by rational protein design". Proc. Natl. Acad. Sci. USA 94:5562-5567, May 1997.
Coldren et al. "The rational design and construction of a cuboidal iron-sulfur protein". Proc. Natl. Acad. Sci. USA 94:6635-6640, Jun. 1997.
Benson et al. "The development of new biotechnologies using metalloprotein design". Curr. Opin Biotechnol. 9(4):370-376, Aug. 1998. Abstract only.
Ueno et al. "Coordinated design of cofactor and active site structures in development of new protein catalysts". J. Am. Chem. Soc. 127(18):6556-6562, May 2005. Abstract only.
Thomas et al. "Artificial metalloenzymes: proteins as hosts for enantioselective catalysis". Chem. Soc. Rev. 34(4):337-346, Apr. 2005. Abstract only.

* cited by examiner

*Primary Examiner*—Chih-Min Kam
(74) *Attorney, Agent, or Firm*—Occhiuti Rohlicek & Tsao LLP

(57) ABSTRACT

Disclosed herein are recombinant copper or zinc binding polypeptides containing at least one copper or zinc binding motif and a sequence heterologous to it. Also disclosed is a method to reduce the concentration of a free copper or zinc ion in a substrate by contacting it with a recombinant polypeptide containing a copper or zinc binding motif. A further method relates to reducing the concentration of a free copper or zinc ion in a substrate by contacting it with a host cell that expresses a recombinant polypeptide containing a copper or zinc binding motif.

16 Claims, No Drawings

SEQUENCE LISTING

<160> NUMBER OF SEQ ID NOS: 12

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      exemplary peptide motif
<220> FEATURE:
<221> NAME/KEY: MOD_RES
<222> LOCATION: (2)..(8)
<223> OTHER INFORMATION: any one of the 20 biologically occurring amino
      acids

<400> SEQUENCE: 1

His Xaa Xaa Xaa Xaa Xaa Xaa Xaa His
 1               5

<210> SEQ ID NO 2
<211> LENGTH: 14
<212> TYPE: PRT
<213> ORGANISM: Artificial Sequence
<220> FEATURE:
<223> OTHER INFORMATION: Description of Artificial Sequence: Synthetic
      exemplary peptide motif
<220> FEATURE:
<221> NAME/KEY: MOD_RES
<222> LOCATION: (2)..(13)
<223> OTHER INFORMATION: any one of the 20 biologically occurring amino
      acids

<400> SEQUENCE: 2

His Xaa Xaa Xaa Xaa Xaa Xaa Xaa Xaa Xaa Xaa Xaa Xaa His
 1               5                   10

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      exemplary peptide motif
<220> FEATURE:
<221> NAME/KEY: MOD_RES
<222> LOCATION: (2)..(6)
<223> OTHER INFORMATION: any one of the 20 biologically occurring amino
      acids

<400> SEQUENCE: 3

His Xaa Xaa Xaa Xaa Xaa Met
 1               5

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      exemplary peptide motif
<220> FEATURE:
<221> NAME/KEY: MOD_RES
<222> LOCATION: (2)..(7)
<223> OTHER INFORMATION: any one of the 20 biologically occurring amino
      acids

<400> SEQUENCE: 4

Met Xaa Xaa Xaa Xaa Xaa Xaa His
 1               5

```
<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      exemplary peptide motif
<220> FEATURE:
<221> NAME/KEY: MOD_RES
<222> LOCATION: (2)..(4)
<223> OTHER INFORMATION: any one of the 20 biologically occurring amino
      acids

<400> SEQUENCE: 5

His Xaa Xaa Xaa Cys
 1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      exemplary peptide motif
<220> FEATURE:
<221> NAME/KEY: MOD_RES
<222> LOCATION: (2)..(6)
<223> OTHER INFORMATION: any one of the 20 biologically occurring amino
      acids

<400> SEQUENCE: 6

His Xaa Xaa Xaa Xaa Xaa His
 1               5

<210> SEQ ID NO 7
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Phe His Gly Arg Ala Asp Ala Leu Leu His Lys Ile
 1               5                  10

<210> SEQ ID NO 8
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Glu Asn His Val Phe Ala Asp Ala Ile Gly His His Ile
 1               5                  10

<210> SEQ ID NO 9
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Phe Leu Gly Arg Ala Asp Ala Leu Leu Leu Lys Ile
```

-continued

```
<210> SEQ ID NO 10
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Glu Asn Leu Val Phe Ala Asp Ala Ile Gly Leu His Ile
  1               5                  10

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

His Gly Arg Ala Asp Ala Leu Leu His
  1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

His Val Phe Ala Asp Ala Ile Gly His
  1               5
```

METAL-BINDING MOTIF COMPOSITIONS AND METHODS

BACKGROUND

Metal ions such as copper and zinc are indispensable cofactors in the chemistry of living systems. For example, copper, with two oxidation states Cu(I) and Cu(II), is critical to cellular redox reactions. In plants, copper-binding proteins utilize this metal as a co-factor in diverse biochemical pathways, e.g., photosynthesis, respiration, oxidative stress response, and ethylene signaling. Yet, while copper and other metal ions are pivotal to cellular biochemistry, they lead to the production of highly destructive hydroxyl radicals when present in excessive concentrations. In fact, no free copper ions are found in cells, as they are chelated either by low-molecular weight compounds (e.g., nicotinamine) or by copper-binding proteins (e.g., metallothionein).

To date, several studies have identified short sequence metal-binding motifs. These can be exploited, vis-à-vis the chemically reactive properties of metal ions, to develop enzymes having improved or new catalytic properties. Such novel enzymes can be used in a variety of industrial or biomedical applications. Polypeptides containing metal binding motifs can also be used for chelating metal ions to reduce their free concentrations in metal-contaminated substrates, e.g., industrial waste, soil, or water, in an economically and ecologically sound way. For this purpose, metal binding polypeptides can be added directly to a contaminated substrate, or alternatively, transgenic cells that express metal-binding polypeptides can be used for bioremediation.

SUMMARY

The present invention is based, in part, on the discovery of novel copper or zinc-binding (CZB) amino acid sequence motifs in *Arabidopsis*. Copies of these short motifs can be heterologously introduced into naturally occurring polypeptide sequences or polypeptide sequences designed de novo, or into any combination of such sequences to create novel copper or zinc binding recombinant CZB polypeptides (CZBPs), e.g., copper-modulated enzymes. In addition, polypeptides containing CZB motifs, or cells that express them, can be used to reduce the concentration of copper or zinc in a substrate (e.g., contaminated soil or water).

Accordingly, one aspect of the invention relates to a copper or zinc-binding recombinant polypeptide containing at least one copy (e.g., two or three copies) of a CZB motif as described herein and one or both of a first adjacent amino acid sequence containing the amino terminus of the polypeptide and a second adjacent amino acid sequence containing the carboxy terminus of the polypeptide. The last 70%, 50%, 30%, or 10% of the first amino acid sequence or the first 70%, 50%, 30%, or 10% of the second amino acid sequence are heterologous to the at least one copy of the CZB motif. The term "last," as just used above in reference to the first amino acid sequence, is defined starting from the amino terminus of the recombinant polypeptide and ending at the residue preceding the at least one motif. The term "first," as just used above in reference to the second amino acid sequence, is defined starting from the first amino acid following the at least one motif and ending at the carboxy terminus of the recombinant polypeptide. Where the recombinant polypeptide includes multiple copies of a CZB motif, they can be identical or different from each other.

Another aspect of the invention relates to an antibody that is directed against any of the above-described recombinant polypeptides and binds to the at least one CZB motif contained therein.

A further aspect of the invention relates to an isolated nucleic acid encoding any of the above-described recombinant polypeptides.

Yet another aspect of the invention relates to a method for reducing the concentration of a free copper or zinc ion in a substrate. The method includes contacting a substrate suspected of containing a free copper or zinc ion with a recombinant polypeptide containing at least one CZB motif. The recombinant polypeptide can be one that contains heterologous sequences. Not that the method can also include determining a concentration of the free copper or zinc ion after contact with the recombinant polypeptide.

In a related aspect, the concentration of a free copper or zinc ion in a substrate can be reduced by contacting the substrate with a host cell that expresses a recombinant polypeptide containing at least one CZB motif. After contacting the substrate with the host cell, the cells are allowed to take up the free copper or zinc ion, whereby intracellular complexes are formed between the recombinant polypeptide and the copper or zinc ion. As a result, the concentration of free copper or zinc ion in the substrate is reduced.

Other features or advantages of the present invention will be apparent from the following detailed description, and also from the claims.

DETAILED DESCRIPTION

Novel CZBPs are described herein. In addition, a method for reducing free copper or zinc ion concentrations in a substrate by contact with a CZBP is also described.

A CZB motif is a short amino acid sequence motif capable of binding to copper or zinc. A CZB motif can used in the CZBPs described herein can be any of the following:

$$\text{His-}X_1\text{-}X_2\text{-}X_3\text{-}X_4\text{-}X_5\text{-}X_6\text{-}X_7\text{-His} \quad \text{(SEQ ID NO: 1)}$$

$$\text{His-}X_1\text{-}X_2\text{-}X_3\text{-}X_4\text{-}X_5\text{-}X_6\text{-}X_7\text{-}X_8\text{-}X_9\text{-}X_{10}\text{-}X_{11}\text{-}X_{12}\text{-His} \quad \text{(SEQ ID NO: 2)}$$

$$\text{His }X_1\text{-}X_2\text{-}X_3\text{-}X_4\text{-}X_5\text{-}X_6\text{-Met} \quad \text{(SEQ ID NO: 3)}$$

$$\text{Met-}X_1\text{-}X_2\text{-}X_3\text{-}X_4\text{-}X_5\text{-}X_6\text{-}X_7\text{-His} \quad \text{(SEQ ID NO: 4)}$$

$$\text{His-}X_1\text{-}X_2\text{-}X_3\text{-Cys} \quad \text{(SEQ ID NO: 5)}$$

Amino acids at the degenerate "X" positions can be any of the 20 biologically occurring amino acids, i.e., alanine, arginine, aspartate, asparagine, cysteine glutamate, glutamine, glycine, histidine, isoleucine, leucine, lysine, methionine, phenylalanine, proline, serine, threonine, tryptophan, tyrosine, or valine. One or more copies of any of the above CZB motifs can be introduced into a host polypeptide sequence to generate a copper or zinc-binding protein having an enhanced or novel enzymatic activity.

The recombinant CZBPs described herein contain at least one copy of any of SEQ ID NOs:1-5 and one or both of a first adjacent amino acid sequence containing the amino terminus of the polypeptide and a second adjacent amino acid sequence containing the carboxy terminus of the polypeptide, where the last 70% of the first amino acid sequence (e.g., any value between 5-70%) and the first 70% of the second amino acid sequence (e.g., any value between 5-70%) are both heterologous to the at least one copy.

The term "recombinant" as used herein refers to any polypeptide encoded by an isolated nucleic acid, i.e., a nucleic acid not found in its naturally occurring genomic locus. The phrase "heterologous to the at least one copy," as used herein, means that the referred-to first or second amino sequence is not found to adjoin the at least one copy in any naturally occurring amino acid sequence.

The ability of CZBPs to bind copper or zinc can be tested, e.g., by assaying retention of the CZBP on a copper or zinc ion affinity chromatography substrate such as copper-chelated to Chelating Sepharose Fast Flow resin (Amersham Biosciences, Uppsala, Sweden). Alternatively, a difference spectrum (at 220-800 nm) can be determined for the polypeptide-metal versus polypeptide alone.

Nucleic acids encoding polypeptides containing one or more copies of any of the above CZB motifs can be readily generated using standard recombinant DNA techniques. See, e.g., *Current Protocols in Molecular Biology* (2005):3.16-3.17.

As CZB motif sequences are relatively short, they are most conveniently encoded by oligonucleotides. Oligonucleotides are typically synthesized chemically according to the solid phase phosphoramidite triester method described by Beaucage and Caruthers (1981), Tetrahedron Letts., 22(20):1859-1862, e.g., using an automated synthesizer, as described in Needham-VanDevanter et al. (1984) Nucleic Acids Res., 12:6159-6168. A wide variety of equipment is commercially available for automated oligonucleotide synthesis.

Nucleic acids can also be custom ordered from a variety of commercial sources, such as Sigma-Genosys; The Midland Certified Reagent Company, The Great American Gene Company, ExpressGen Inc., Operon Technologies Inc. (Alameda, Calif.) and many others. Generally such nucleic acids will be incorporated into a nucleic acid vector (e.g., a plasmid) and propagated in a host cell (e.g., an *E. coli* cell).

The nucleic acids encoding CZBPs can be codon-optimized for expression in a particular cell type (e.g., in a plant cell, a fungal cell, a mammalian cell, a yeast cell, or a bacterial cell). Codon usage frequency tables are publicly available, e.g., on the world wide web.

In determining where to introduce CZB motifs in a host sequence, it is important to consider, when available, the three dimensional structure of the host protein. The three dimensional structures of as many as 32,000 proteins are known and available publicly, e.g., in the protein data banks available on the internet through the world wide protein data bank. The "Metalloprotein Database and Browser," (available on the world wide web) is particularly useful for examining the three dimensional structures of known metalloproteins. However, even without experimentally determined structural data for a polypeptide sequence of interest, e.g., a sequence generated de novo, valuable inferences about its likely structure can be gleaned by computational structural analysis. Useful programs for structure prediction from an amino acid sequence include, e.g., the "SCRATCH Protein Predictor" suite of programs available to the public on the world wide web.

Protein rational design algorithms, such as "DEZYMER," developed by Homme Hellinga of Duke University are particularly useful for determining the CZB motifs described herein within a host sequence so as to optimize catalytic activity of the introduced metal center without destabilizing the secondary or tertiary structure of the host protein. See, e.g., Hellinga & Richards (1991) *J. Mol. Biol.* 222:763-785 and U.S. patent application Ser. Nos. 10/840,796 and 10/914,573. Indeed, a number of examples of rationally designed metalloenzymes using the DEZYMER algorithm are known in the art. For example, a bacterial thioredoxin protein naturally devoid of any metal binding activity was modified to contain an iron active site able to catalyze the dismutation of superoxide anion, i.e., a novel catalytic function for thioredoxin. See Pinto et al. (1997), *Proc. Natl. Acad. Sci USA,* 94:5562-5567 and Benson et al. (2000), *Proc Natl. Acad. Sci. USA,* 97:6292-6297.

It is important that introduction of a CZB motif in a host sequence (e.g., an enzyme) not destabilize the known or predicted secondary structure of the polypeptide to be modified. Accordingly, the known or predicted secondary structure of the polypeptide and the position of its functional domains (e.g., a catalytic site) inform the choice of an optimal position for inserting a CZB motif.

The structural effect of inserting a CZB motif at any given location in an enzyme polypeptide sequence can be readily tested, e.g., by phage display expression analysis methods that are commonly known in the art. Failure of a polypeptide to fold properly will generally preclude its display on a phage coat. The effect of CZB motif insertion on enzyme activity can be tested by an appropriate functional assay to determine, e.g., $K_m$, $V_{max}$, and sensitivity to copper or zinc ion concentrations.

Examples of polypeptides that can be modified by introducing CZB motifs include bacterial indole-3-acetyl-L-aspartic acid hydrolase, superoxide dismutase, glyoxylase II, jack bean urease, zinc finger transcription factors, or zinc metalloproteases to name a few.

Antibodies can be generated to bind specifically to a CZB motif within the context of a specific CZBP. Such antibodies are useful, e.g., to down-regulate a copper or zinc dependent enzymatic activity of a CZBP by preventing copper or zinc ions from binding to CZB motifs. Methods for generating antibodies are well known in the art. See, e.g., Harlow et al., Antibodies: A Laboratory Manual, Cold Spring Harbor Laboratory, Cold Spring Harbor, N.Y., 353-355 (1988).

A free copper or zinc ion concentration in a substrate (e.g., contaminated soil, water, or industrial waste) can be reduced in a substrate suspected of containing free copper or zinc ions by contacting the substrate with a composition that contains an isolated polypeptide having one or more of the CZB motifs described herein. The CZB motif-containing polypeptides can be naturally occurring polypeptides or polypeptides containing heterologous sequences as described above. Preferably, after contacting the substrate with the composition containing the CZB motif, the concentration of the free copper or zinc ion in the substrate is then assayed after removal of the protein-metal complex (e.g., by immunoprecipitation). A number of analytical methods are known in the art for measuring the concentrations of free metal concentrations in solution, e.g., atomic absorption spectrometry.

Alternatively, as a form of bioremediation, free copper or zinc ion concentrations can be reduced in a substrate by contacting it with host cells that express a recombinant heterologous CZBP as described herein. The host cells can be, e.g., bacterial, plant, fungal, or mammalian. Preferably, the efficacy of the bioremediation can be determined assaying the free concentration of copper or zinc ions after contacting the substrate with the CZBP-expressing host cells.

The following specific examples are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

Identification of CZB Motif-Containing Proteins in *Arabidopsis thaliana*

At the whole plant level, the root is the frontier in metal ion uptake and therefore plays a crucial role in metal homeostasis. In this study, we conducted the first unbiased screening for copper-binding proteins in *Arabidopsis* roots. Immobilized metal affinity chromatography (IMAC) combined with mass spectrometry (MS) was employed to identify putative Cu and Zn-binding proteins in *Arabidopsis* roots. We examined the individual metalloproteomes of Cu and Zn in *Arabidopsis* roots on IMAC and two-dimensional gel electrophoresis.

Harvested root tissues were ground to powder with a mortar and pestle in liquid nitrogen. Proteins were extracted with binding buffer (20 mM sodium phosphate, pH 5.8, 500 mM NaCl, 0.1% (w/v) Triton X-100 containing 1 mM phenylmethyl sulfonyl fluoride). The crude extract was centrifuged at 16,000×g at 4° C. for 10 minutes, and the supernatant was ready for IMAC. Protein concentrations were determined by the Bradford method (Bio-Rad, Hercules, Calif., USA), with BSA used as a standard.

IMAC was performed with Chelating Sepharose Fast Flow resin (Amersham Biosciences, Uppsala, Sweden) to separate metal-binding proteins according to the manufacturer's instructions, with minor modifications as described below. A 0.4 ml bed volume of resin of was transferred into a 2 ml tube and washed 5 times, for 4 minutes each, with 1 ml of water. The coupling reaction was performed by adding 0.5 ml of water or 0.2 M divalent metal ions, Cu(II) and Zn(II), to compose null-, Cu- and Zn-IMAC resins, respectively. The coupled resin washed 5 times, for 4 minutes each, with 1 ml of water and equilibrated with 1 ml of binding buffer for 4 min. Eighteen milligrams of *Arabidopsis* root proteins were applied to the resin and incubated for 60 minutes at 4° C. with gentle shaking. The resin washed thoroughly with 1 ml of binding buffer containing 10 mM imidazole 6 times, for 4 minutes each, to remove non-specifically bound proteins. The specifically-bound proteins were then eluted with a buffer (pH 5.5) containing 10 mM sodium acetate, 500 mM NaCl, and 40 mM imidazole.

To determine the strength and specificity of interactions between the proteins and Cu-IMAC, two alternative elution protocols were employed. After non-specifically bound proteins were washed off with binding buffer containing 10 mM imidazole, proteins were eluted sequentially with elution buffer containing 25 mM imidazole, elution buffer containing 40 mM imidazole and sodium dodecyl sulfate (SDS) buffer (62.5 mM Tris-HCl, pH 6.8, 3% (w/v) SDS, 10% (v/v) glycerol) or elution buffer containing 2 mM of the divalent metal ions Cu(II), Cd(II), Mg(II) or Zn(II).

The proteins eluted from IMAC were precipitated with 10% (w/v) trichloracetic acid and washed with 80% (v/v) ice-cold acetone 5 times to remove contaminants and then lyophilized before being subjected to 2-DE separation.

The lyophilized protein samples were dissolved with rehydration buffer (7 M urea, 2 M thiourea, 2% w/v), CHAPS, 0.5% (v/v), Triton X-100, 0.7% (w/v) dithiothreitol, and 0.5% (v/v) IPG buffer). Two hundred micrograms of proteins (for Coomassie Brilliant Blue R-250 staining) or 50 pg of proteins (for silver staining; PlusOne Silver Staining Kit, Protein, Amersham Biosciences) were applied to 18-cm pH 4-7 immobilized pH gradient (IPG) strips with rehydration loading followed by isoelectric fusing with use of IPGphor (Amersham Biosciences). Isoelectric focusing was performed in 6 steps (150 V for 10 min, 250 V for 20 min, 500 V for 30 min, 1,000 V for 30 min, gradient from 1,000 V to 8,000 V in 60 min and 8,000 V for 24,000 Vh) at 20° C. The focused IPG strips were then equilibrated with 10 ml equilibration buffer (62.5 mM Tris, 10% (v/v) glycerol, 5% (v/v) 2-mercaptoethanol, 2.3% (w/v) SDS) 3 times for 10 min each and then resolved on vertical SDS-PAGE gels with use of a PROTEAN II xi electrophoresis kit (Bio-Rad). Gels were visualized by silver or Coomassie Blue staining.

The Coomassie Blue-stained protein spots were manually excised for in-gel digestion. Excised protein spots were reduced with 65 mM dithioerythntol in 25 mM ammonium bicarbonate, pH 8.5, at 37° C. for 1 hour, alkylated with 100 mM iodoacetamide in 25 mM ammonium bicarbonate, pH 8.5, in the dark at room temperature for 1 hour. The gel piece was destained twice with 50% (v/v) acetonitrile (ACN) in 25 mM ammonium bicarbonate, pH 8.5, for 15 min each, dehydrated with ACN for 5 minutes, dried, and subsequently digested with 100 ng of sequencing grade, modified trypsin (Promega, Madison, Wis., USA) in 10 µl of 25 mM ammonium bicarbonate, pH 8.5, at 37° C. for 16 hours. The tryptic peptides were then extracted for 15 min twice with 50% (v/v) ACN, 5% (v/v) trifluoroacetic acid with moderate sonication. After vacuum evaporation of ACN, the peptides were redissolved in 10 µl of 0.1% (v/v) formic acid.

Tryptic peptides were subjected to concerted MALDI peptide mass fingerprinting (PMF) and collision-induced dissociation MSIMS analysis for protein identification with use of a dedicated QTOF Ultima MALDI instrument (Micromass, Manchester, UK) at the Core Facilities for Proteomics Research, Academia Sinica. Peptides were identified by searching the mass profiles of the NCBI nr database with the search engine Mascot (available on the internet at matrixscience.com). The following parameters were used for the search: *Arabidopsis thaliana* (thale cress), trypsin, up to 1 missed cleavage, carbamidomethylation of cysteine and oxidation of methionine, peptide tolerance 50 ppm, MSIMS tolerance 0.2 Da, mass values MH$^+$ and monoisotopic, and peptide charge 1$^+$.

The amino acid sequences of all identified proteins (see Table 1 below) were bulk downloaded from TAIR Analysis Tools, which is found on the world wide web. The 29,162 *Arabidopsis* predicted protein sequences were downloaded from TAIR FTP Downloads with the file name ATH_pep_cm_20040228.

TABLE 1

Proteins Identified by Cu-IMAC

| Protein Name | GenBank Accession No. |
| --- | --- |
| Ribulose Bisphosphate Carboxylase Small Chain 1A | P10795 |
| Major Latex Protein-Related | AAK63869 |
| ADP-ribosylation factor, putative | AAT41759 |
| Glutathione Transferase, Putative | P42760 |
| Dehyxroxyascorbate Reductase, Putative | NP_173387 |
| Glutathione Transferase | NP_180643 |
| Superoxide Dismutase (Fe) | B39267 |
| Short-Chain Dehydrogenase/Reductase (SDR) | AAO42826 |
| Myrosinase Binding Protein, putative | NP_188263 |
| Jasmonate Inducible Protein Isolog | NP_188264 |
| Ca$^{2+}$-Dependent Membrane Binding Protein Annexin | NP_174810 |
| Adenosine Kinase 1 | NP_187593 |
| pfkB Type Carbohydrate Kinase | NP_195950 |
| Putative Glutamine Synthetase | AAO42253 |
| Glutamine Synthetase, Cytosolic Enzyme | AAL84997 |

TABLE 1-continued

Proteins Identified by Cu-IMAC

| Protein Name | GenBank Accession No. |
|---|---|
| Glutamine Synthetase-Related | NP_176794 |
| Actin 8 | NP_175350 |
| S-adenosylmethionine synthetase-Related | NP_181225 |
| S-adenosylmethionine synthetase 2 | NP_192094 |
| Isocitrate Dehydrogenase, Putative | NP_176768 |
| Elongation Factor 1B-gamma | NP_176084 |
| Enolase (2-phospho-D-glycerate hydrolase) | NP_181192 |
| S-adenosyl-L-homocysteine hydrolase | CAB09795 |
| Glycosyl Hydrolase Family 1 | NP_187537 |
| $H^+$-Transporting ATP Synthetase β Chain (mitochondrial) | NP_568204 |
| $H^+$-Transporting ATP Synthetase β Chain | NP_680155 |
| 10-Formyltetrahydrofolate Synthetase | NP_564571 |
| Jacalin Lectin Family | NP_188267 |
| 5-methyltetrahydropteroyltriglutamate-homocysteine S-methyltransferase | NP_197294 |
| Elongation Factor 2 | A96602 |
| Aconitate Hydratase | NP_567763 |

Copper-binding motifs characterized to date can be classified into 4 types, types I to III and a fourth atypical type, according to their binding geometry and spectroscopic properties. In types I and III, prediction of binding motifs cannot be built on short sequence rules such as those described below. According to protein structures solved so far, in type II and the atypical binding geometry, the amino acids that serve as copper ligands are more likely to occur continuously or within a small distance. The atypical copper binding motifs were reported to form linear bicoordination with copper via the C—$(X)_2$—C motif (where X stands for any amino acid residue).

Smith et al. (*J Proteome Res.* 2004 July-August; 3(4):834-40) used a similar Cu-IMAC approach to isolate copper-binding proteins in human liver cells; the 9 putative metal-binding domains, H—(X)n-H (n=0-5) and C(X)nC (n=2-4), were present in most of their Cu-IMAC-isolated binding proteins. Thus, we analyzed the presence of these 9 motifs in our Cu-IMAC isolated protein set. To filter out random occurrences of these motifs, the presence of these motifs in the whole *Arabidopsis* proteome of 29,162 predicted loci was also examined. These 9 motifs are present in 29 of 35 (83%) of our Cu-IMAC binding proteins. However, 20,780 of 29,162 predicted proteins (71%) in the *Arabidopsis* proteome also contain these 9 motifs. Since this difference in the frequency of presence between the proteins eluted by Cu-IMAC and the whole *Arabidopsis* proteome is not significant, we therefore performed an expanded survey.

Cysteine, methionine and histidine have been reported to have high affinity to divalent metal ions. Several attempts have been made to characterize the conserved metal binding motifs, and the lengths of these motifs usually range from 2 to 10 or more amino acid residues. Thus, we examined putative copper-binding motifs of 2 conserved amino acids with high metal affinity separated by a fixed distance ranging from 0 to 12 residues. All 9 combinations of the three amino acids Cys, Met and/or His and 13 distance variations constitute 117 potential metal-binding motifs, i.e.: C—$(X)_n$—C, C—$(X)_n$—H, C—$(X)_n$-M, H—$(X)_n$—C, H—$(X)_n$—H, H—$(X)_n$-M, M-$(X)_n$—C, M-$(X)_n$—H, and M-$(X)_n$-M, where n=0-12.

The amino acid sequences of all identified proteins in this study were used as a positive reference set, and the 29,162 whole *Arabidopsis* proteome sequences sewed as a background reference set. The presence of the 117 motifs in the positive and whole *Arabidopsis* proteome sets were analyzed and compared. Twenty-three motifs showed higher frequency of occurrence in the positive reference set than in the whole *Arabidopsis* proteome, with the presence of H—$(X)_{12}$—H (SEQ ID NO:2) being the most statistically significant. Since it is estimated that up to one-third of all proteins and enzymes contain metal ions in their structure, using the whole proteome as the background may lead to underestimation of significance; therefore, the cutoff number needs to be adjusted. To find a significant cutoff value for the 23 candidate motifs, the motifs were ranked according to the significance of difference in the Cu-IMAC protein set and in the *Arabidopsis* proteome. The cumulative sums of protein numbers covered by the 23 motifs in the Cu-IMAC protein set and in the *Arabidopsis* proteome were analyzed. The top 6 significant motifs, H—$(X)_5$—H (SEQ ID NO:6), H—$(X)_7$—H (SEQ ID NO:1), H—$(X)_{12}$—H (SEQ ID NO:2), H—$(X)_6$-M (SEQ ID NO:3), M-$(X)_7$—H (SEQ ID NO:4), and H—$(X)_3$—C (SEQ ID NO: 5), were selected, since they were found in 89% of the proteins identified in the Cu-IMAC protein set. In contrast, only 58% of the proteins in the *Arabidopsis* proteome contained the 6 motifs. The significantly higher occurrence of these 6 sequences in the Cu-IMAC protein set suggested that they are likely copper-binding motifs.

Synthesis and Testing of CZB Motif-Containing Peptides

Peptides containing the motif H—$(X)_7$—H (SEQ ID NO: 1) were selected according to the native sequence of GenBank NP_188264 and GenBank AAK63869 (see Table 1) to yield WT3g (GFHGRADALLHKI (SEQ ID NO: 7)) and WT4g (ENHVFADAIGHHI (SEQ ID NO: 8)), respectively. In WT3g and WT4g, the CZB motifs are HGRADALLH and HVFADAIGH (SEQ ID NO: 11 and 12), respectively. The corresponding peptides with amino acid substitution (His to Leu) were also designed to yield mt3g (GFLGRADALLLKI (SEQ ID NO: 9)) and mt4g (ENLVFADAIGLHI (SEQ ID NO: 10)). All four peptides were commercially synthesized and purified by Genesis Biotech, Inc. (Taipei, Taiwan). Peptides (500 μM) were incubated with buffer containing 500 μM CuSO4, 20 mM Tris buffer, pH 6.8, for 15 mm before measurement of absorption spectra as described in Zou et al. (*Biometals.* 2005 February; 18(1):63-74). Absorption spectra (221 nm to 800 nm) were measured by spectrophotometry (NanoDrop ND-1000, Wilmington, Del., USA). The difference spectra were obtained by subtracting spectra for the peptide-metal complex with the one for peptide only.

The UV absorption spectra of both WT3g and WT4g were shifted upon addition of Cu(II), which was indicative of conformation changes induced by metal binding as described in, e.g., Zou et al. (*Biometals.* 2005 February; 18(1):63-74).

When both histidine residues in the H—$(X)_7$—H (SEQ ID NO: 1) were mutagenized to leucine residues as in peptides mt3g and mt4g, their copper-binding ability was greatly compromised or abolished. These results strongly suggested that a motif containing H—$(X)_7$—H (SEQ ID NO: 1) can bind Cu(II). Further, these results also corroborate the value of identifying metal-binding motifs via a proteomic survey as described herein.

OTHER EMBODIMENTS

All of the features disclosed in this specification may be combined in any combination. Each feature disclosed in this specification may be replaced by an alternative feature serving the same, equivalent, or similar purpose.

From the above description, one skilled in the art can easily ascertain the essential characteristics of the present invention, and without departing from the spirit and scope thereof, can make various changes and modifications of the invention to adapt it to various usages and conditions. Thus, other embodiments are also contemplated.

What is claimed is:

1. A recombinant polypeptide comprising at least one copy of a copper or zinc binding motif, and one or both of a first adjacent amino acid sequence containing the amino terminus of the polypeptide and a second adjacent amino acid sequence containing the carboxy terminus of the polypeptide, wherein the last 70% of the first adjacent amino acid sequence and the first 70% of the second adjacent amino acid sequence are not found to adjoin the copper or zinc binding motif in a naturally occurring amino acid sequence; and the polypeptide binds a copper or zinc ion, and wherein the recombinant polypeptide includes the sequence of SEQ ID NO: 7 or 8 and the copper or zinc binding motif has the sequence of SEQ ID NO: 11 or 12.

2. The recombinant polypeptide of claim 1, wherein the polypeptide comprises the first adjacent amino acid sequence.

3. The recombinant polypeptide of claim 2, wherein the last 50% of the first adjacent amino acid sequence is not found to adjoin the copper or zinc binding motif in a naturally occurring amino acid sequence.

4. The recombinant polypeptide of claim 3, wherein the last 30% of the first adjacent amino acid sequence is not found to adjoin the copper or zinc binding motif in a naturally occurring amino acid sequence.

5. The recombinant polypeptide of claim 4, wherein the last 10% of the first adjacent amino acid sequence is not found to adjoin the copper or zinc binding motif in a naturally occurring amino acid sequence.

6. The recombinant polypeptide of claim 1, wherein the polypeptide comprises the second adjacent amino acid sequence.

7. The recombinant polypeptide of claim 6, wherein the first 50% of the second adjacent amino acid sequence is not found to adjoin the copper or zinc binding motif in a naturally occurring amino acid sequence.

8. The recombinant polypeptide of claim 7, wherein the first 30% of the second adjacent amino acid sequence is not found to adjoin the copper or zinc binding motif in a naturally occurring amino acid sequence.

9. The recombinant polypeptide of claim 8, wherein the first 10% of the second adjacent amino acid sequence is not found to adjoin the copper or zinc binding motif in a naturally occurring amino acid sequence.

10. The recombinant polypeptide of claim 1, wherein the polypeptide comprises the first and second adjacent amino acid sequences.

11. The recombinant polypeptide of claim 1, wherein the recombinant polypeptide comprises at least two copies of the copper or zinc binding motif.

12. The recombinant polypeptide of claim 11, wherein the two copies are different from each other.

13. The recombinant polypeptide of claim 12, wherein the recombinant polypeptide comprises at least three copies of any of SEQ ID NOs: 11 and 12.

14. The recombinant polypeptide of claim 1, wherein the first adjacent amino acid sequence is obtained from a bacterial indole-3-acetyl-L-aspartic acid hydrolase, superoxide dismutase, glyoxylase II, jack bean urease, zinc finger transcription factor, or zinc metalloprotease.

15. The recombinant polypeptide of claim 1, wherein the second adjacent amino acid sequence is obtained from a bacterial indole-3-acetyl-L-aspartic acid hydrolase, superoxide dismutase, glyoxylase II, jack bean urease, zinc finger transcription factor, or zinc metalloprotease.

16. A recombinant polypeptide comprising at least one copy of a copper or zinc binding motif, and one or both of a first adjacent amino acid sequence containing the amino terminus of the polypeptide and a second adjacent amino acid sequence containing the carboxy terminus of the polypeptide, wherein the first adjacent amino acid sequence or the second adjacent amino acid sequence is (1) heterologous to the copper or zinc binding motif and (2) different from a sequence that adjoins the copper or zinc binding motif in a naturally occurring protein; and the polypeptide binds a copper or zinc ion, and wherein the recombinant polypeptide includes the sequence of SEQ ID NO: 7 or 8 and the copper or zinc binding motif has the sequence of SEQ ID NO: 11 or 12.

* * * * *